US011992623B2

(12) United States Patent
Fritz

(10) Patent No.: US 11,992,623 B2
(45) Date of Patent: May 28, 2024

(54) HANDHELD ELECTRONIC DEVICE FOR TEACHING BREATHING TECHNIQUES TO REDUCE STRESS

(71) Applicant: Stacy Fritz, Towson, MD (US)

(72) Inventor: Stacy Fritz, Towson, MD (US)

( * ) Notice: Subject to any disclaimer, the term of this patent is extended or adjusted under 35 U.S.C. 154(b) by 0 days.

(21) Appl. No.: 18/382,792

(22) Filed: Oct. 23, 2023

(65) Prior Publication Data

US 2024/0131299 A1 Apr. 25, 2024

Related U.S. Application Data

(60) Provisional application No. 63/418,775, filed on Oct. 24, 2022.

(51) Int. Cl.
*A61M 21/02* (2006.01)
*A61M 21/00* (2006.01)

(52) U.S. Cl.
CPC ..... *A61M 21/02* (2013.01); *A61M 2021/0022* (2013.01); *A61M 2021/0044* (2013.01); *A61M 2021/0066* (2013.01); *A61M 2021/0088* (2013.01); *A61M 2205/502* (2013.01); *A61M 2205/582* (2013.01); *A61M 2205/584* (2013.01); *A61M 2205/8206* (2013.01); *A61M 2205/8237* (2013.01); *A61M 2209/084* (2013.01)

(58) Field of Classification Search
CPC ................................................ A61M 21/00–02
See application file for complete search history.

(56) References Cited

U.S. PATENT DOCUMENTS

| | | | | |
|---|---|---|---|---|
| 2013/0310636 A1* | 11/2013 | Krans | ............... | A61B 5/486 |
| | | | | 600/26 |
| 2018/0374381 A1* | 12/2018 | Darmour | ........... | A61B 5/02055 |
| 2019/0307983 A1* | 10/2019 | Goldman | ............... | A61B 5/165 |
| 2023/0096515 A1* | 3/2023 | McDevitt | ................ | A61B 5/01 |
| | | | | 600/28 |

FOREIGN PATENT DOCUMENTS

WO WO-2011045709 A1 * 4/2011 ......... A61B 5/02416

* cited by examiner

*Primary Examiner* — Thaddeus B Cox
(74) *Attorney, Agent, or Firm* — Dale J. Ream

(57) ABSTRACT

A handheld electronic device is actuated by a user to energize selected colored lights and vibrations according to predetermined intensities and patterns that are associated with predetermined breathing patterns. The handheld electronic device uses multiple haptic inputs that engage associated sensory receptors of a person, namely, visual sensations, vibration sensations, and smell, a.k.a. aroma therapy.

19 Claims, 19 Drawing Sheets

PROGRAM 0
STANDBY MODE: POWER IS ON BUT NO BREATHING EXERCISE. LIGHT ONLY. NO VIBRATION
COLOR: LIGHT BLUE (0,128,255)

| TIME | MAGNITUDE |
|---|---|
| 0 | 0 |
| 4 | 1 |
| 8 | 0 |

PROGRAM 1
BREATH TECHNIQUE: EQUAL RATIO BREATING, LIGHT AND VIBRATION
COLOR: WHITE (255,255,255)

| TIME | MAGNITUDE |
|---|---|
| 0 | 0 |
| 4 | 1 |
| 8 | 0 |

PROGRAM 2
BREATH TECHNIQUE: BOX BREATH, LIGHT AND VIBRATION
COLOR: AMBER YELLOW (255,230,0)

| TIME | MAGNITUDE |
|------|-----------|
| 0    | 0         |
| 4    | 1         |
| 8    | 1         |
| 12   | 0         |

PROGRAM 3
BREATH TECHNIQUE: 4-7-8 TECHNIQUE, LIGHT AND VIBRATION
COLOR: PALE BLUE (153,255,255)

| TIME | MAGNITUDE |
|------|-----------|
| 0 | 0 |
| 4 | 1 |
| 11 | 1 |
| 19 | 0 |

PROGRAM 4
BREATH TECHNIQUE: LION'S BREATH, LIGHT AND VIBRATION
COLOR: BRIGHT ORANGE (255,164,0)

| TIME | MAGNITUDE |
|------|-----------|
| 0    | 0         |
| 4    | 1         |
| 12   | 1         |
| 12   | 0         |

HANDHELD ELECTRONIC DEVICE FOR TEACHING BREATHING TECHNIQUES TO REDUCE STRESS

REFERENCE TO RELATED APPLICATIONS

This application is a non-provisional application that claims the priority of provisional patent application 63/418,775 filed Oct. 24, 2022 entitled Handheld Electronic Device for Teaching Breathing Techniques to Reduce Stress, which is incorporated in its entirety in the present application.

BACKGROUND OF THE INVENTION

This invention relates generally to handheld devices that promote wellness or fitness to a user.

Studies increasingly show that experiencing stress in one's personal life and work experience can have a very negative impact on one's health. For instance, work-related stress may lead to physical problems such as immune deficiency disorders, musculoskeletal disorders, gastrointestinal disorders such as irritable bowel syndrome, and sleep deficiency. Workplace stress also has adverse effects on workers' mental health, with an increased risk of anxiety, burnout, depression, and substance abuse disorders. Workers who are stressed at work are more likely to engage in unhealthy behaviors, such as cigarette smoking, alcohol and drug abuse, and poor dietary patterns.

Various activities and techniques have been proposed in the prior art for relieving the effects of stress. For instance, it has been recommended that stress may be reduced by the person engaging in regular physical activity, maintaining a healthy diet, improving one's sleep pattern, meditation, or even counseling. Although each of these methods or combinations of them are presumably effective, many people still need a more immediate, timely, and repeatable solution that may be employed anywhere and anytime, such as while at work or at home or when a person has only a short window of time to get the impacts of stress under control.

Therefore, it would be desirable to have a handheld device that may be held in a user's hand and, when activated, uses multiple haptic impulses to guide the user through a selected breathing technique specifically designed to settle or counteract the results of stress.

SUMMARY OF THE INVENTION

This invention is directed to a handheld electronic device that teaches proper breathing techniques using visual and vibrational haptic outputs/sensations to signal and teach guided breathing techniques that promote a reduction in stress and its negative effects.

The electronic device may have the appearance of a ball or globe constructed of a translucent or transparent material which defines an interior space in which a plurality of LED lights each having a different color and at least one vibration element along with a PCB (printed circuit board) or controller, is electrically connected to an on/off button and a mode actuator button.

Each single depression of the actuator button interfaces with the internal electronics to actuate a next mode. Each mode is associated with a predetermined colored LED. Accordingly, current is delivered to a selected LED and vibration element and caused to illuminate and vibrate according to a predetermined ramp up procedure.

The LED and vibration unit may be actuated for 1 second at a low intensity, and then one second at a next higher level of intensity, and then one second at yet a next higher level of intensity, and so on, preferably for 4 seconds. Then, a reverse or ramp-down procedure follows, for instance, gradually decreasing a light and vibration intensity at one second intervals until the method is complete.

In another aspect, the electronic device may be powered by a rechargeable battery, such as with a wireless magnetic charging cable in which electric current passes through coiled wires to surround a magnet (known as an inductor) so as to make an electromagnetic capable of passing voltage to a nearby receiver.

In still another aspect, the electronic device includes a base unit configured to hold the LED and vibrational portion and may be configured to dispense the aroma of essential oils as another haptic input intended to reduce the impact of stress.

Therefore, a general object of this invention is to provide a handheld electronic device that may be actuated by a user to energize selected colored lights and vibrations according to predetermined intensities and patterns that are associated with predetermined breathing patterns.

Another object of this invention is to provide a handheld electronic device, as aforesaid, that uses multiple haptic inputs that engage associated sensory receptors of a person, namely, visual sensations, vibration sensations, and smell, a.k.a. aroma therapy.

Still another object of this invention is to provide a, as aforesaid, handheld electronic device that may be activated by a person whenever the person perceives a need or desire to counteract the impacts of stressful conditions.

Other objects and advantages of the present invention will become apparent from the following description taken in connection with the accompanying drawings, wherein is set forth by way of illustration and example, embodiments of this invention.

DESCRIPTION OF THE PREFERRED EMBODIMENT

Figure 1:
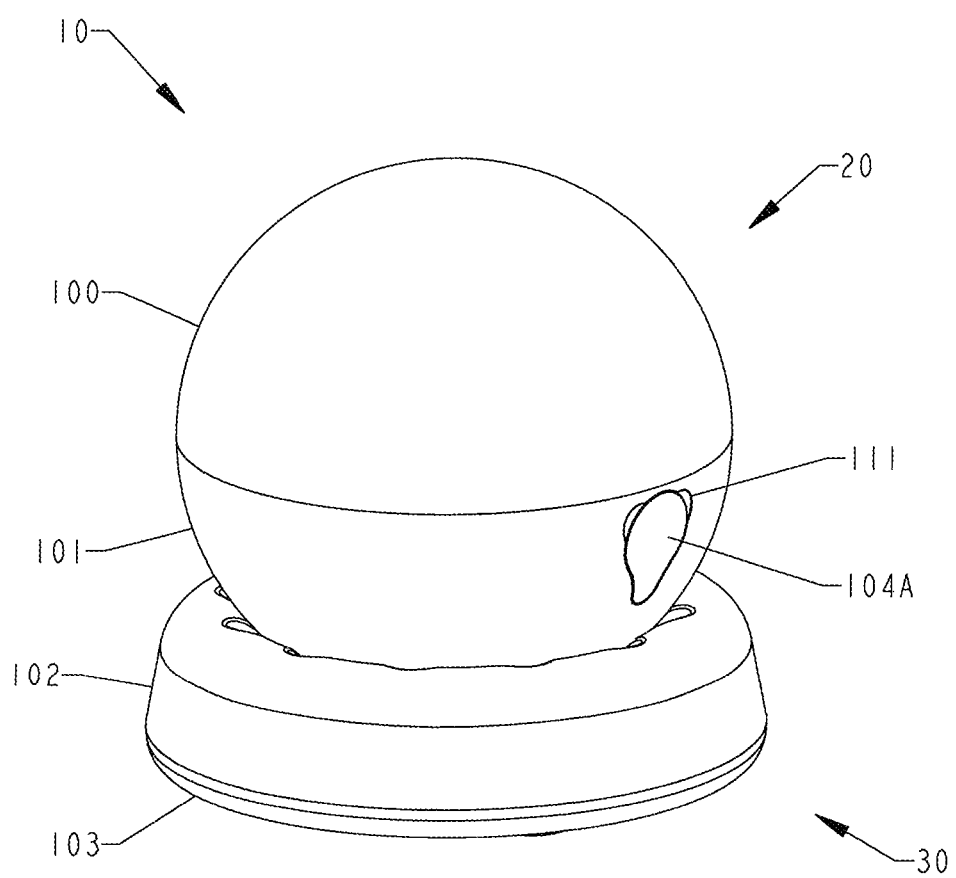
FIG. 1 is a perspective view of a stress relieving apparatus according to a preferred embodiment of the present invention.
Figure 2:
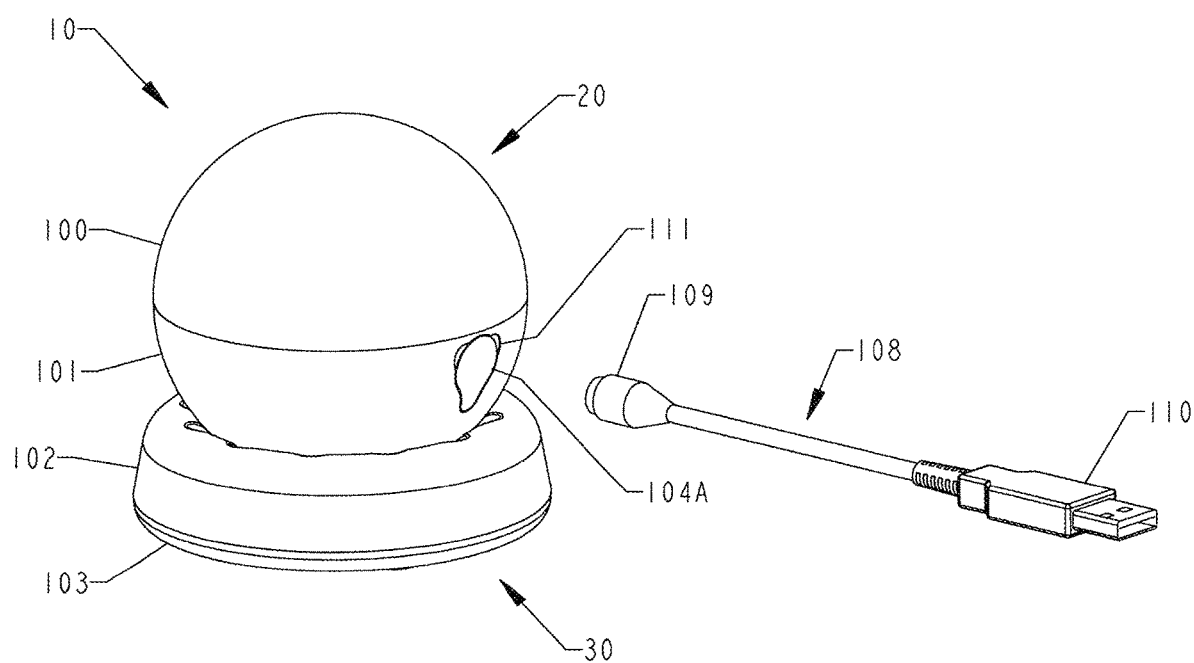
FIG. 2 is another perspective view of the stress relieving apparatus as in FIG. 1, illustrated with a charging cable exploded away from the housing.
Figure 3:
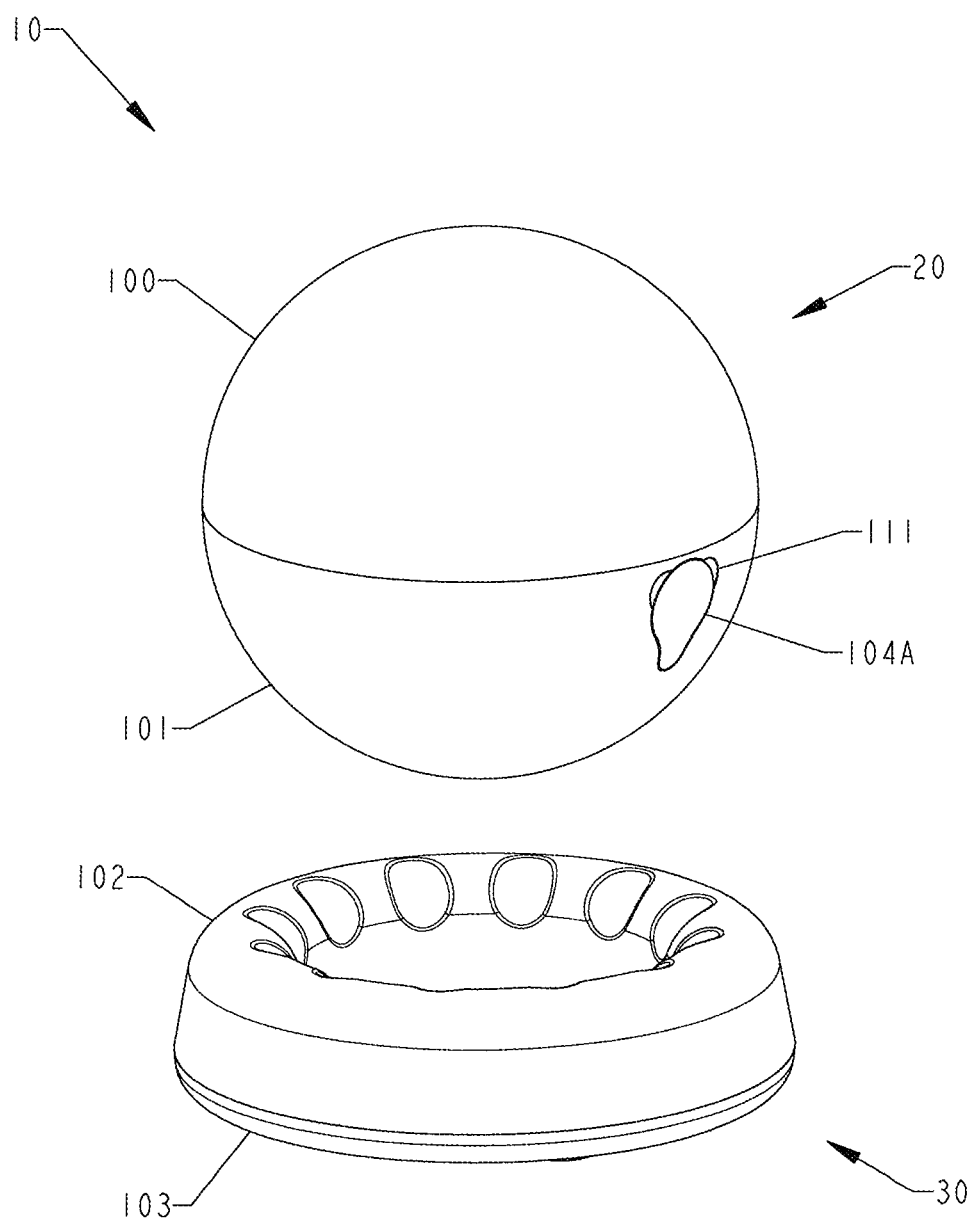
FIG. 3 is a partially exploded view of the apparatus as in FIG. 1, illustrated with the breath ball assembly exploded from the pedestal assembly.
Figure 4:
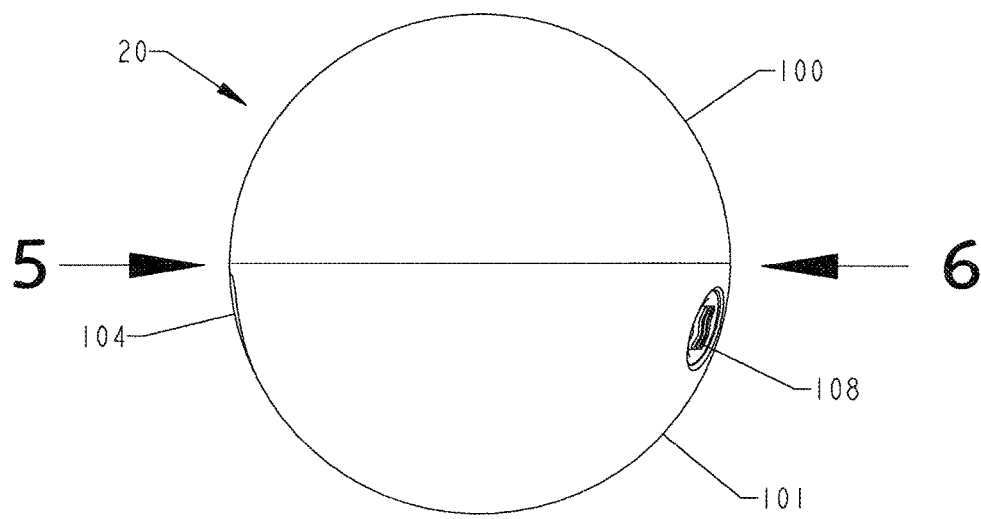
FIG. 4 is a side view of the breath ball assembly illustrated removed from the apparatus as a whole.
Figure 5:
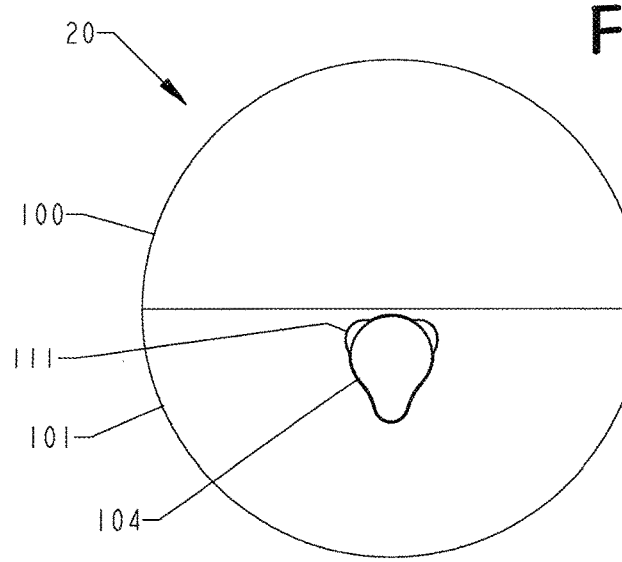
FIG. 5 is a side view of the breath ball assembly as in FIG. 4, illustrated rotated 90°.
Figure 6:
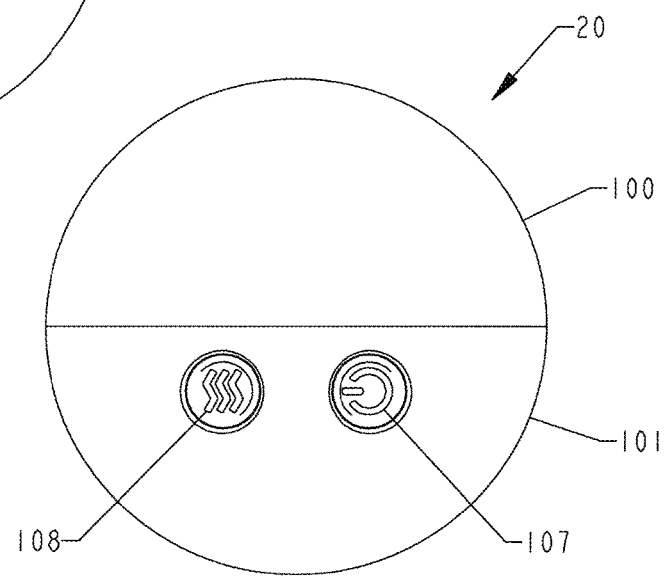
FIG. 6 is another side view of the breath ball assembly as in FIG. 4, illustrated rotated 90° in another direction.

A handheld electronic stress relieving apparatus 10 according to a preferred embodiment of the present invention will now be described with reference to the accompanying drawings. The handheld electronic device includes an LED portion, a vibration portion, an aromatic therapeutic portion, and a processor or controller and non-volatile memory capable of actuating the haptic portions according to a plurality of predetermined breathing techniques.

The electronic stress relieving apparatus 10 may include a housing having a round configuration that is translucent or transparent such that a plurality of colored light emitting diodes may shine through it or illuminate it when energized as will be described in more detail later. In general terms, the first critical aspect of this invention will be referred to as the breath ball assembly 20 which includes a housing having a spherical configuration. Electronic components may be mounted or positioned inside the interior space defined by the housing. For ease of use, the housing may include a lower portion 101 and an upper portion 100 each having a hemispherical configuration and having peripheral edges that are removably coupled together (such as via complementary internal and external threads 128 and 132) so as to be selectively separated if needed for repair or replacement of component parts. When coupled together, the upper and lower portions of the housing define the spherical configuration and interior area.

Figure 12:
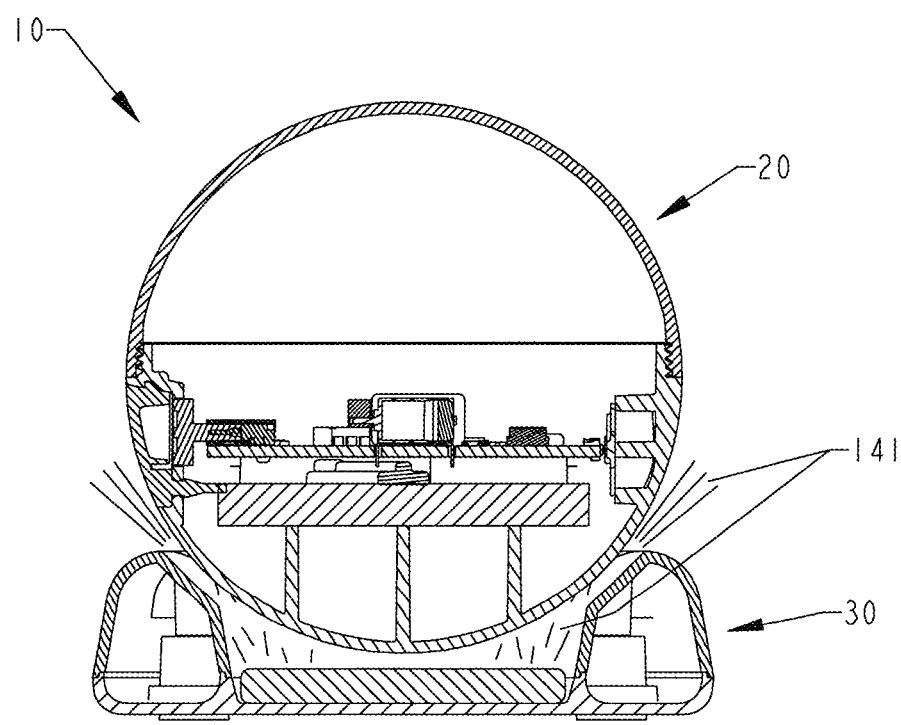
FIG. 12 is a sectional view of the stress relieving apparatus as in FIG. 1.
Figure 13:
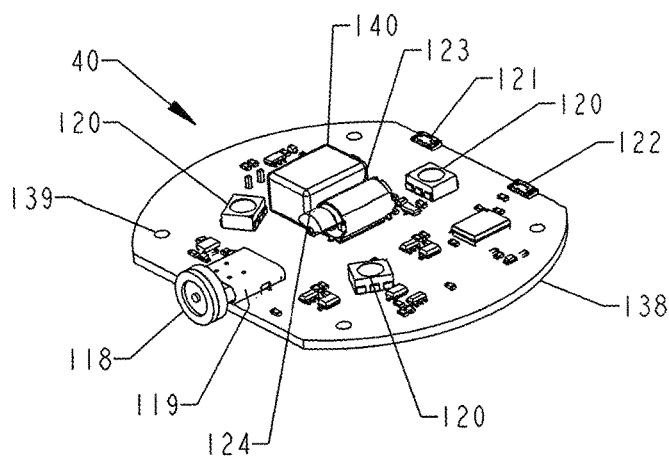
FIG. 13 is a perspective view of the printed circuit board (PCB) as in FIG. 7.
Figure 14:
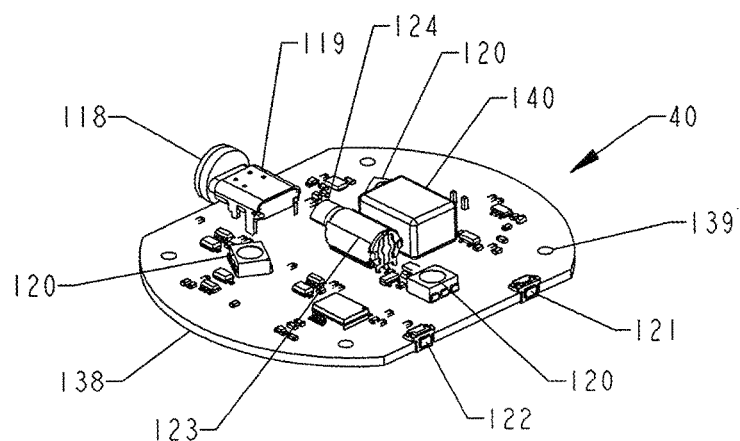
FIG. 14 is another perspective view of the PCB as in FIG. 13 rotated 90°.
Figure 15:
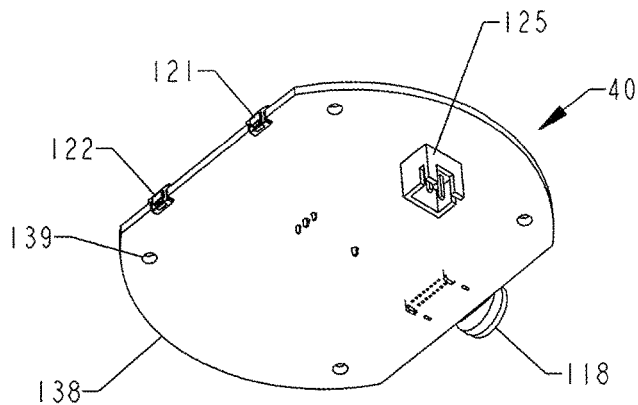
FIG. 15 is a perspective view from a lower side angle of the PCB as in FIG. 14.
Figure 15A:
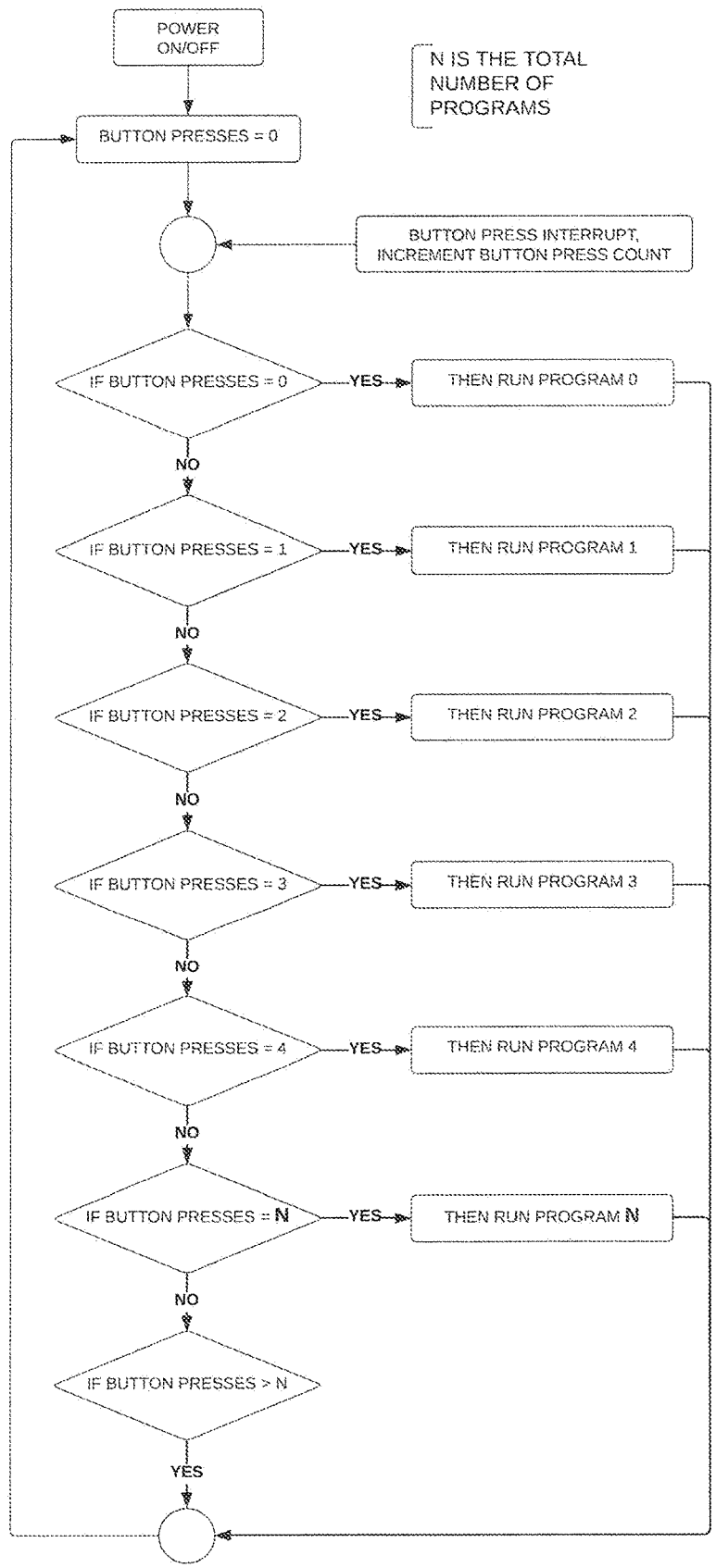
FIG. 15A is a flowchart showing an exemplary method of using the stress relieving apparatus according to the present invention.
Figure 16:
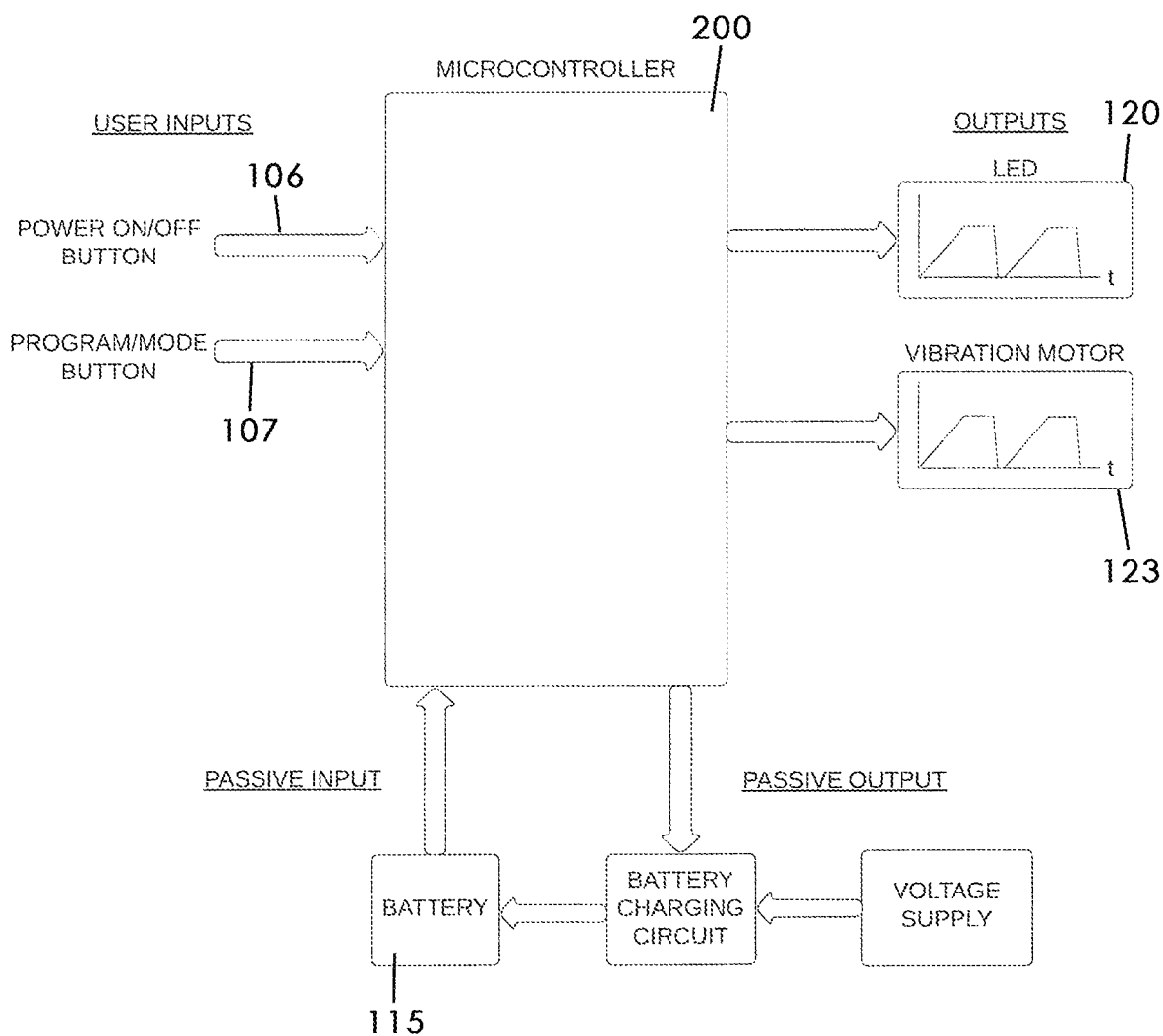
FIG. 16 is a block diagram showing electronic logic components according to a preferred embodiment of the present invention.
Figure 17:
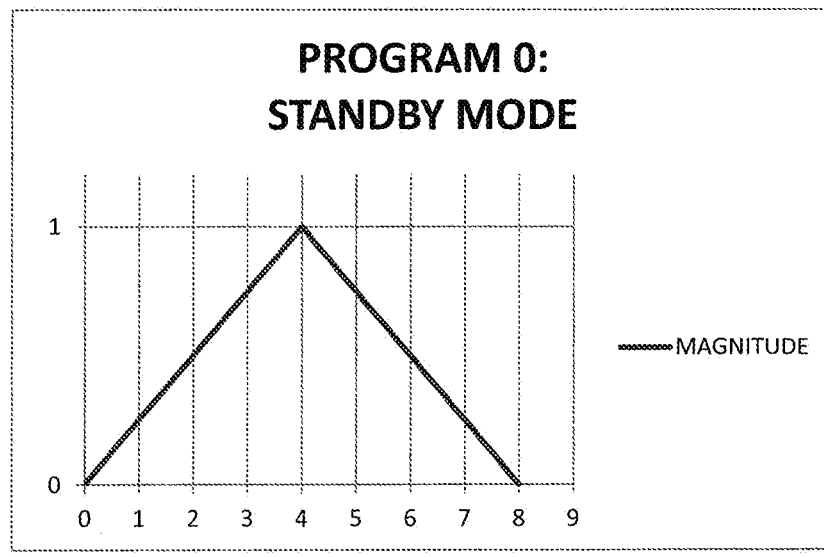
FIG. 17 is a schematic view of a breathing scheme associated with a standby mode according to an embodiment of the present invention.
Figure 18:
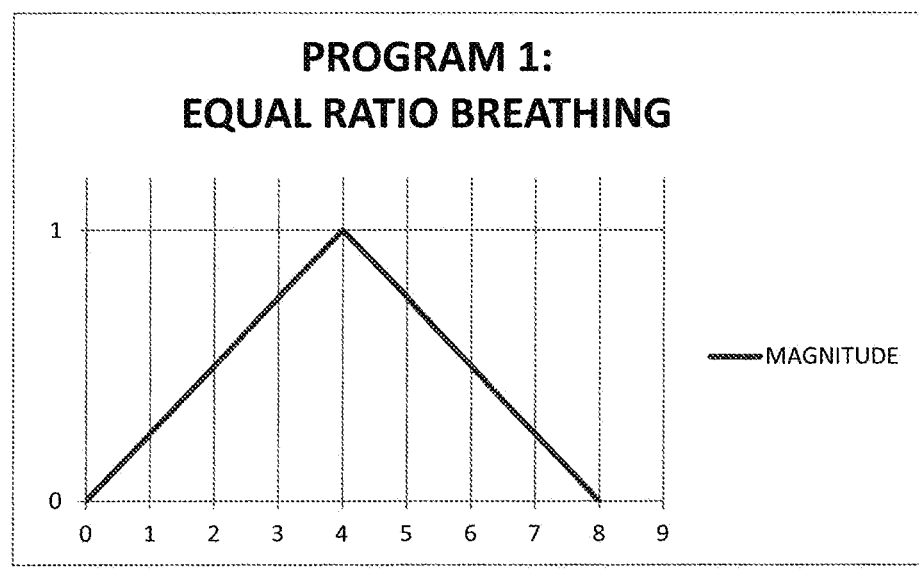
FIG. 18 is a schematic view of a breathing scheme associated with a program 1 mode according to an embodiment of the present invention.
Figure 19:
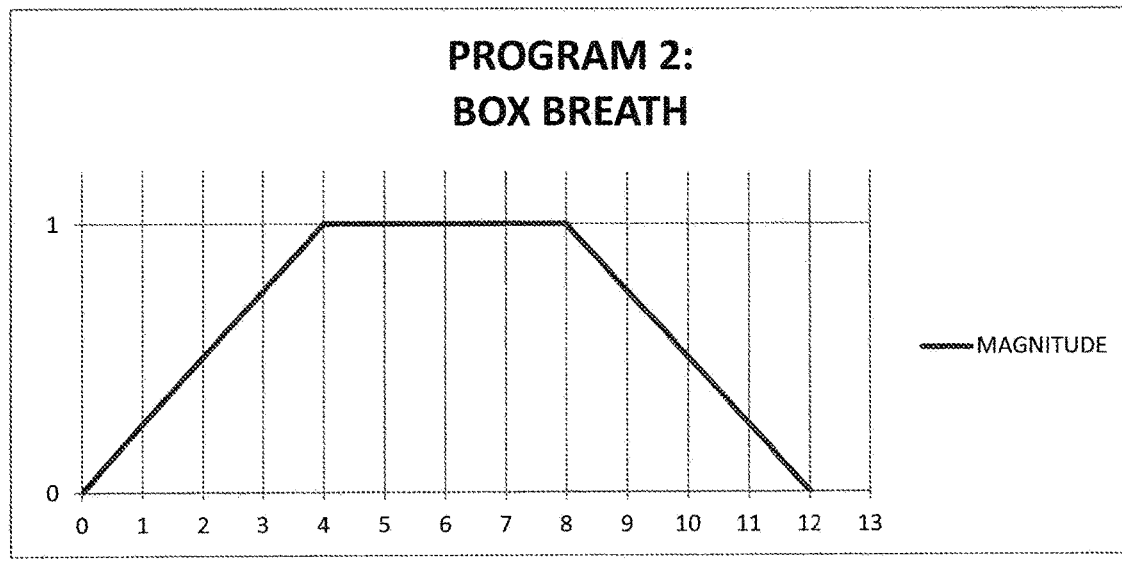
FIG. 19 is a schematic view of a breathing scheme associated with a program 2 mode according to an embodiment of the present invention.
Figure 20:
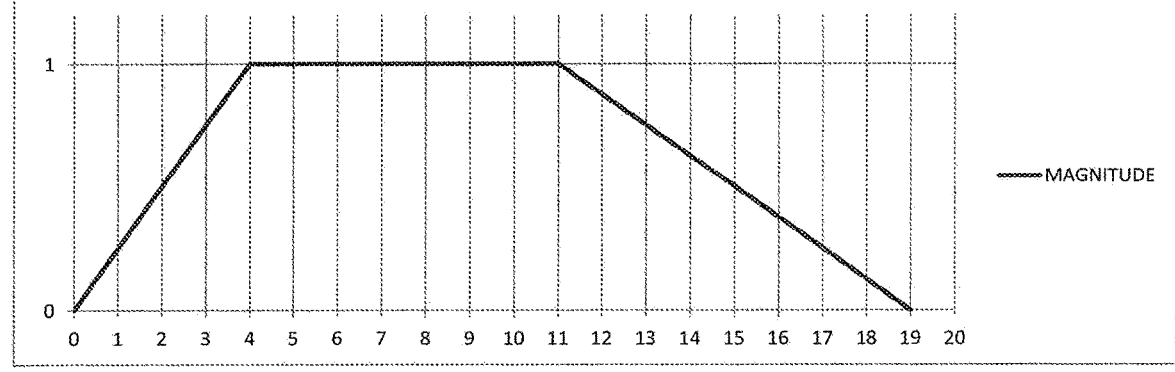
FIG. 20 is a schematic view of a breathing scheme associated with a program 3 mode according to an embodiment of the present invention.
Figure 21:
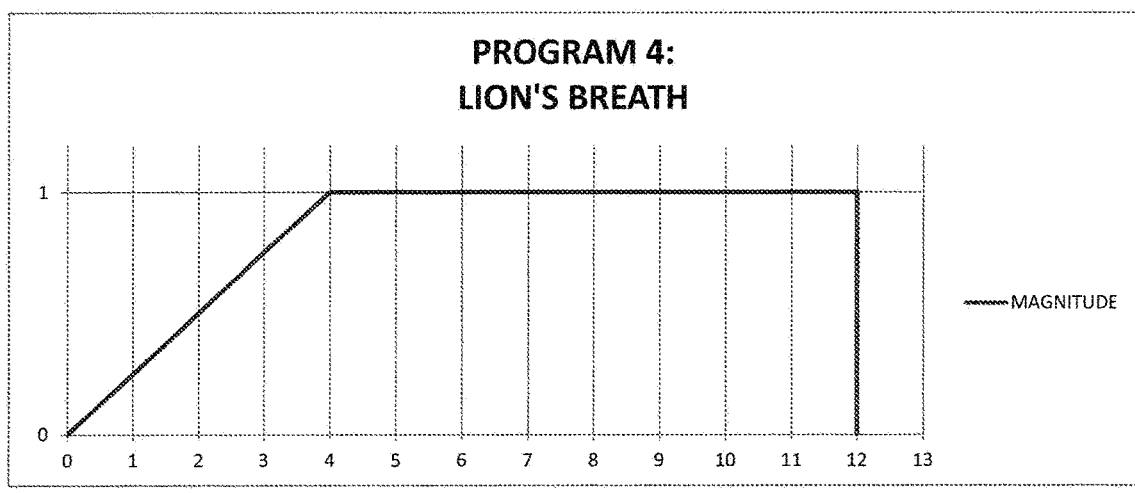
FIG. 21 is a schematic view of a breathing scheme associated with a program 4 mode according to an embodiment of the present invention.
Figure 22:
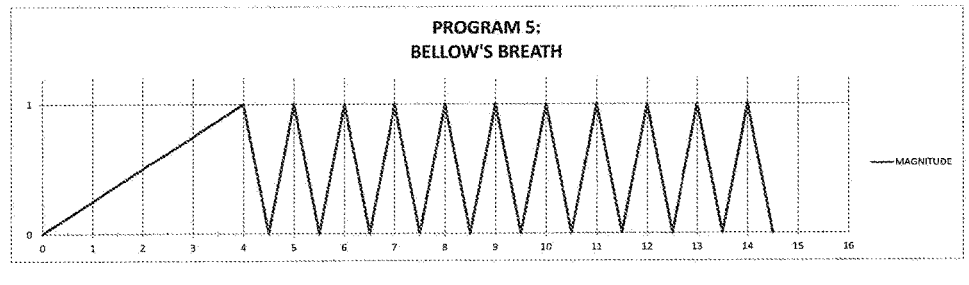
FIG. 22 is a schematic view of a breathing scheme associated with a program 5 mode according to an embodiment of the present invention.

In a critical aspect, the stress relieving apparatus may include pedestal assembly 30 having a base member 103 and an upper portion 102 extending upwardly therefrom, the upper portion 102 having a top surface that defines a recessed area or cut out configured to comfortably receive the hemispherical lower housing 101 in a nested or seated arrangement. The specific reference to FIG. 12, the upper portion 102 includes an inner wall that is downwardly and inwardly sloped or beveled toward the recessed area so as to receive a closed and of the lower housing portion 101 in a nested configuration. Stated geometrically, the inner wall includes an upper edge having a diameter that is, on the one hand, smaller than a diameter of an open end of the lower housing 101 and, on the other hand, larger than a diameter of the bottommost edge of the closed end of the lower housing 101 such that the lower housing 101 is perfectly nested, the closed end being positioned immediately adjacent to the pumice stone 134. With further reference to FIG. 12, the aroma emanating from the pumice stone 134 is illustrated as straight lines with reference number 141.

Further, the base member 103 may include rubber feet 137 so as to be positioned upon a desk, table, or even be held in the hand of a user. The rubber feet 137 may be attached to the base member 103 using screws 136. The base member 103 may have a bottom plate or at least a ledge, and a body defining a doughnut configuration coupled atop the bottom plate, both of which are capable of receiving a lava disk or pumice stone 134 infused with essential oils. The body may define multiple vent holes or apertures 135 through which aroma from the disk may be circulated or ventilated, especially when heated. It will be understood that the lava disk or pumice stone may be removed and replaced such that the aroma derived therefrom may be varied according to a user's preference. Further, operation of the heating element proximate the pumice stone is intended to enhance the efficiency of diffusion and aromatherapy. As shown in the figures, the heating element is positioned proximate the pumice stone when the lower portion of the housing of the breath ball assembly 20 is nested in the pedestal assembly 30 as described above.

Figure 7:
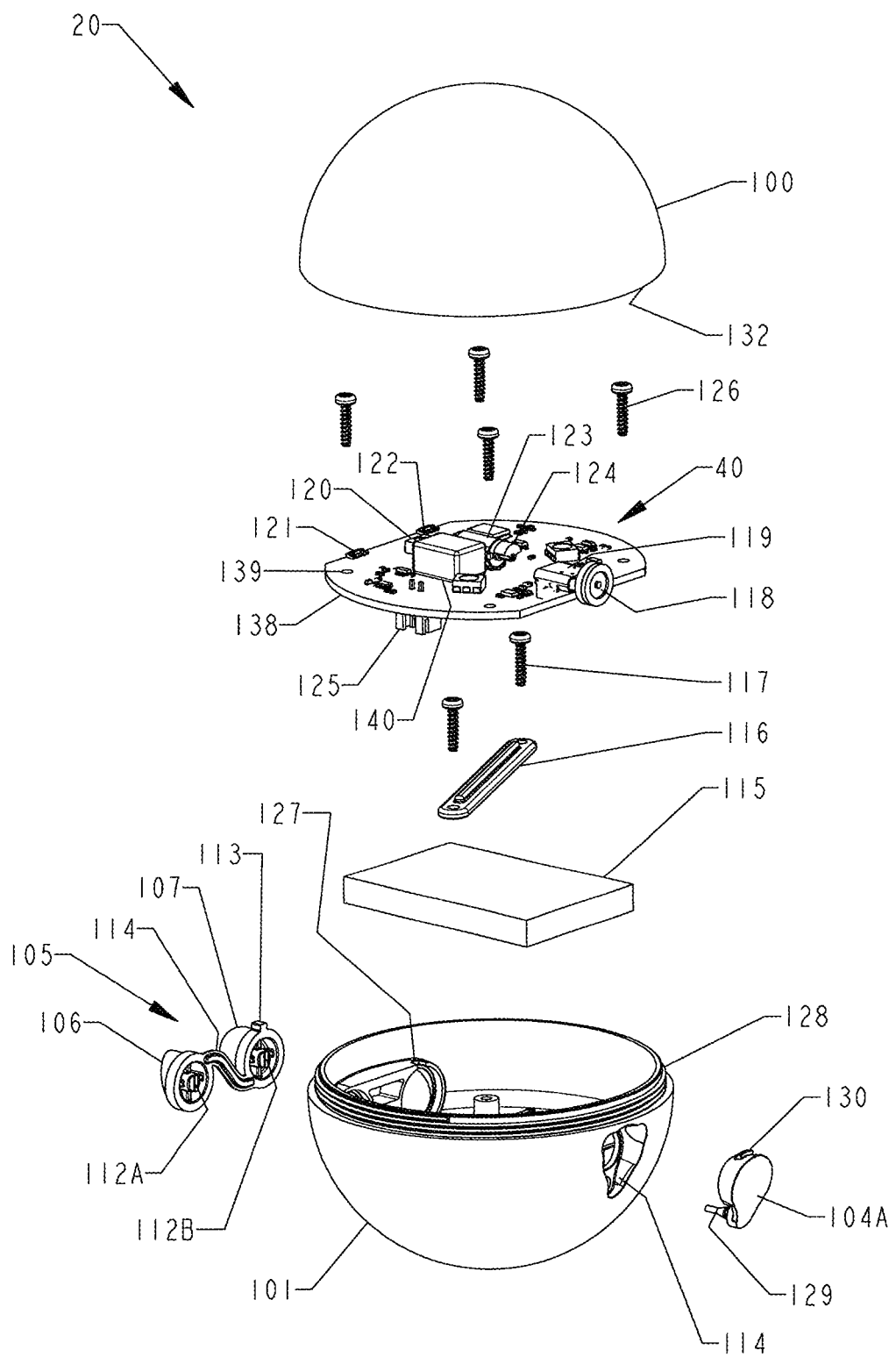
FIG. 7 is an exploded view of the breath ball assembly as in FIG. 4.

A plurality of LED lights 120, a vibration member 123 (i.e., a vibrator motor), the microcontroller 200 (i.e., a processor or equivalent circuitry), memory, and associated electronics may be mounted upon a PCB (printed circuit board) assembly 40 or in electrical communication therewith. Various screws 126 are illustrated for coupling the PCB to the battery 115 and/or respective housing portions 100, 101 (FIG. 7). The battery 115 may be supported upon a plurality of battery ribs 131. Further, the housing may include one or more input buttons 107 in electrical communication with the microcontroller 200 so that the user may select which haptic impulses and modes of operation are desired.

The mounting of electronic components to the PCB assembly 40 is shown most particularly in the exploded view of FIG. 7 which will be described now in more detail. The plurality of LEDs 120 is mounted in a spaced apart pattern atop the PCB assembly 40. Also shown mounted to the PCB are a tactile button for power 121 a tactile button for program/mode 122. The PCB is also referenced using the number 138 along with PCB screw holes 139. The PCB 138 also includes a battery connector 125 configured for electrical communication with the battery 115 when assembled. The heater member 140 is also mounted atop the PCB 138 the vibration member 123 (i.e., vibrator motor) is also mounted atop the PCB 138 along with a counterweight 124. In addition, a USB-C magnetic charging adapter 118 and a USB-C connector are also mounted to the PCB 138.

To be thorough, additional electronics are shown mounted to the lower housing portion 101 in FIG. 7. Namely, reference numerals 112A and 112B refer to the actuator for power button that engage tactile buttons for power on the PCB and program/mode on PCB, respectively. It is understood that these electronics are implementation specific as will be understood by persons of ordinary skill in the art. Further, reference number 127 shows a receiving button index feature on the lower housing portion 101. Reference number 105 refers to an integrated elastomeric main dual button which is comprised of a power button 106, the program/mode button 107 and an index feature 113 that allows respective buttons to be assembled to the lower housing portion 101 in the correct orientation. Reference character 114 is the cavity for receiving a charging port plug 104A. Reference character 129 refers to a charging port umbilical retention stem configured to maintain proper orientation during assembly. It is understood that the lower housing portion 101 may include finger relief cuts or grooves that enhance the ability of a person to grip and peel back the charging port plug 104A.

Figure 8:
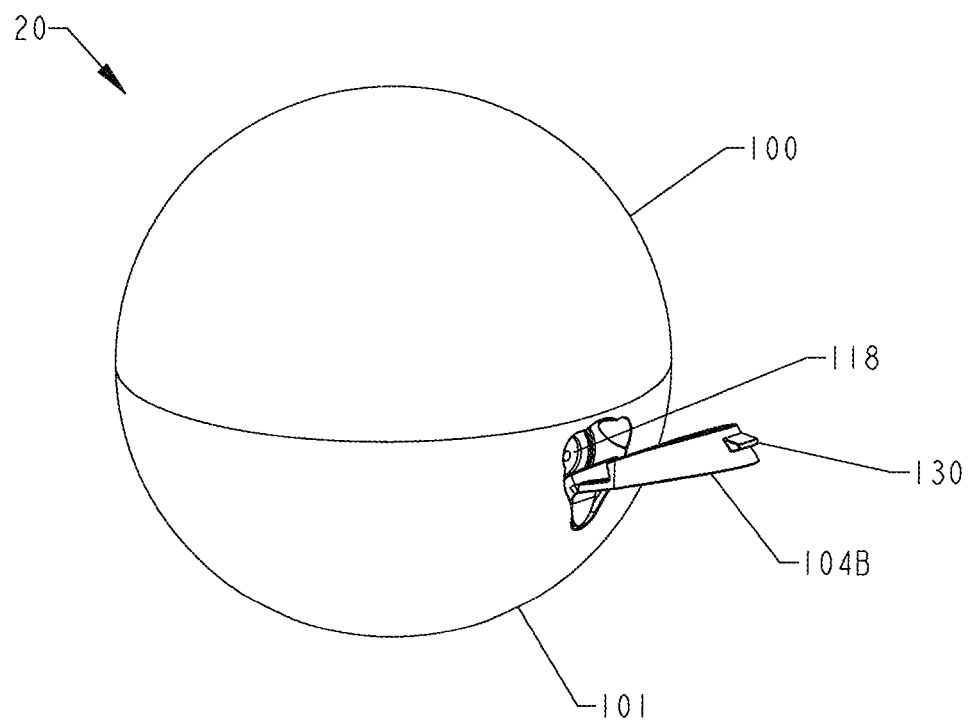
FIG. 8 is a side view of the breath ball assembly as in FIG. 2, illustrated showing a charging cable partially removed from an interior area of the lower housing portion.

With specific reference to FIG. 8, the cavity 114 defined by lower housing portion 101 is shown with the charging port plug 104B shown in its peeled back state along with a snap member 130 that is configured to keep the plug 104B engaged in the cavity 114 until ready for use, i.e., to be "peeled" back. Also, seen in FIG. 8 is the magnetic end, i.e., the USB.

Figure 9:
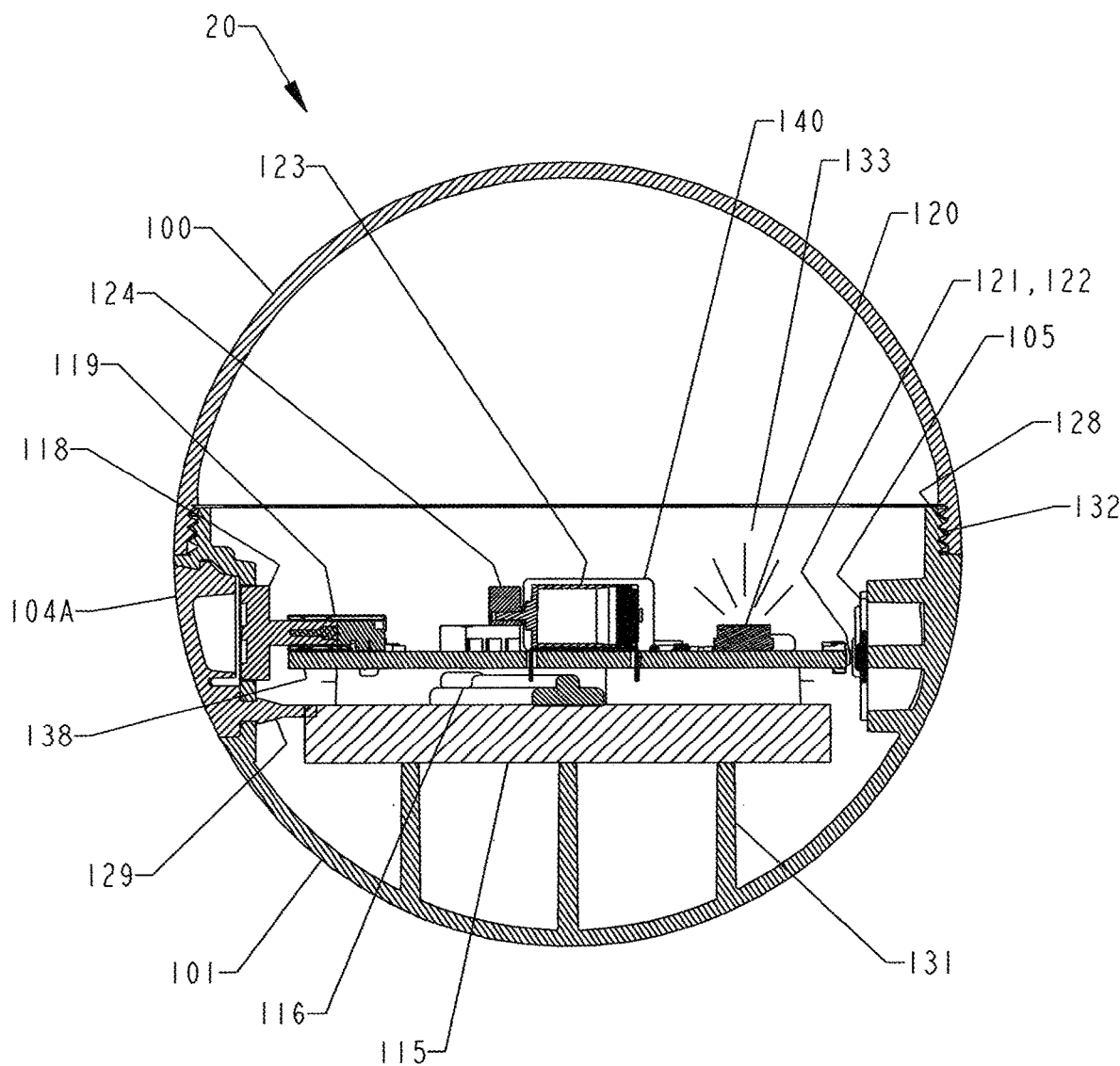
FIG. 9 is a sectional view of the breath ball assembly as in FIG. 3.
Figure 10:
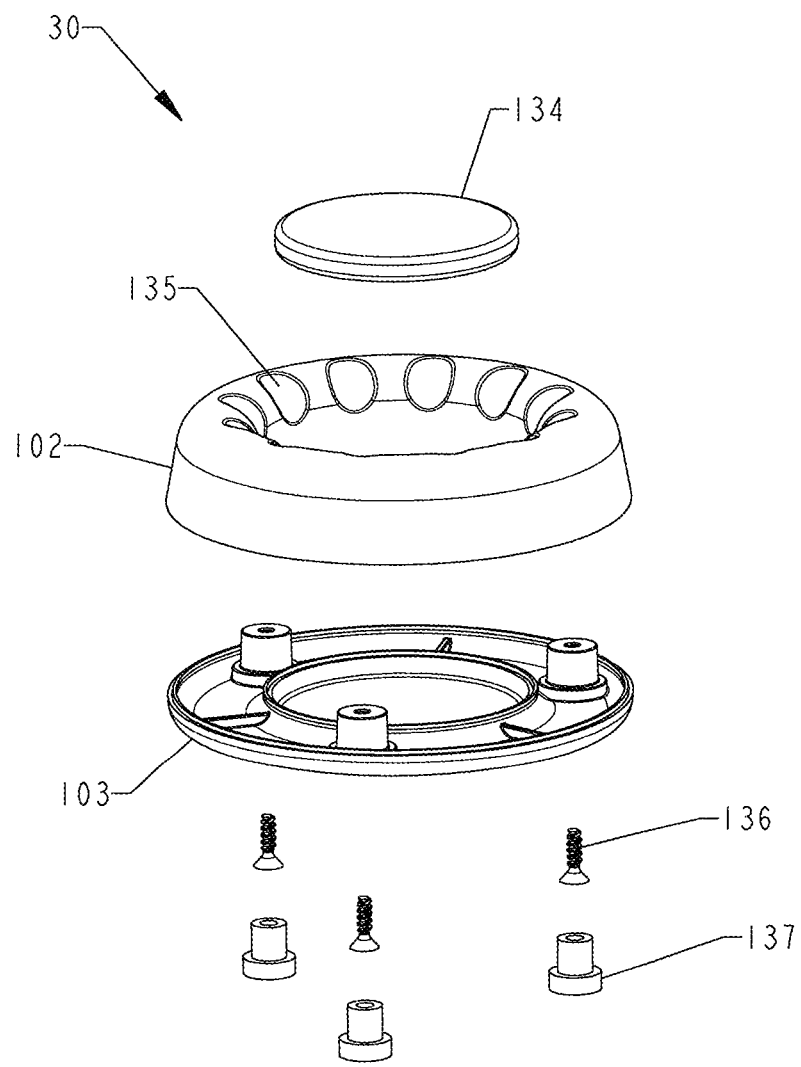
FIG. 10 is an exploded view of the pedestal assembly as in FIG. 3.
Figure 11:
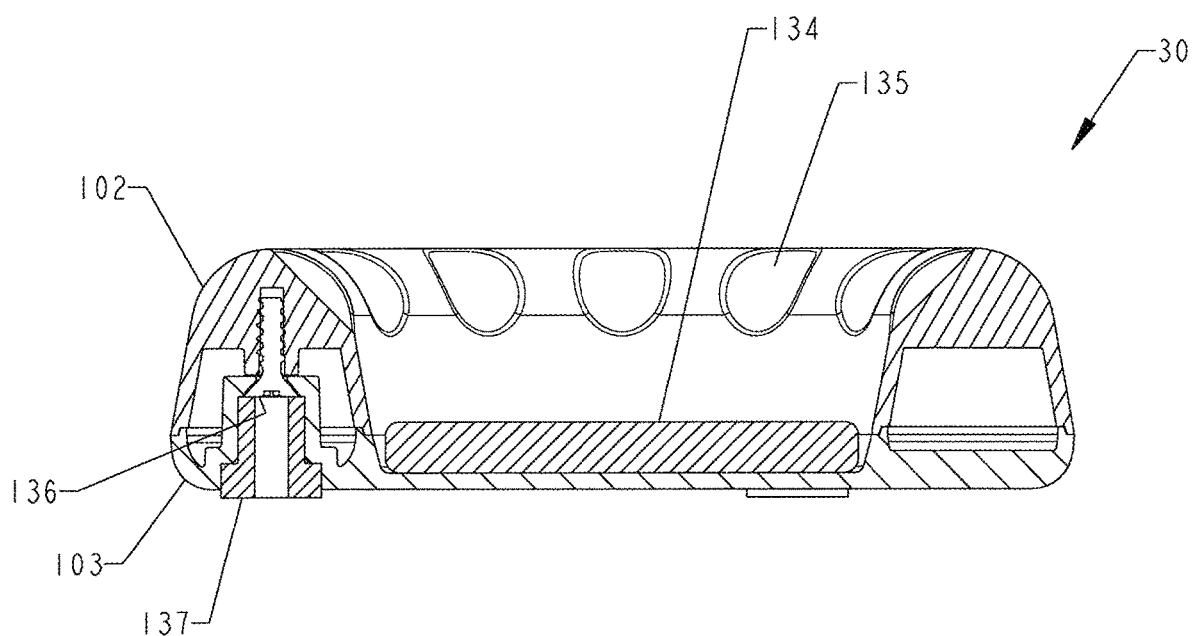
FIG. 11 is a sectional view of the pedestal assembly as in FIG. 10.

In an embodiment, operation of the stress relieving apparatus 10 may be used as described below. Each single depression of the actuator button 107 interfaces with the internal electronics to actuate a next mode. Each mode is associated with a predetermined colored LED (e.g., white, amber/yellow, blue, purple, or combinations thereof). Illumination of an LED is shown using reference number 133 as shown in FIG. 9. Accordingly, current is delivered to a selected LED and vibration element and caused to illuminate and vibrate according to a predetermined ramp up procedure. It is understood that an amount of current may be varied such that an LED or vibration element may be energized to operate at different levels of intensity.

In an exemplary embodiment, the perspective LED 120 and vibration member 123 may be actuated for one second at a low intensity, and then one second at a next higher level of intensity, and then one second at yet a next higher level of intensity, and so on, preferably for four seconds. Then, a reverse or ramp-down procedure follows, for instance, gradually decreasing a light and vibration intensity at one second intervals until the method is complete.

In another exemplary embodiment, a mode of operation is completely correlated with a number of times that the actuation button is pressed. For instance, the electronic device may include a standby mode in which only a single white LED is illuminated when zero actuations of the actuation button are detected. Similarly, the microcontroller may be programmed to energize an amber/yellow LED along with the vibration member when the actuation button is pressed once. Further still, a mode in which a pale blue LED is energized along with the vibration member may be entered when the actuation button is pressed twice. Likewise, depression of the actuation button three times may result in a note in which a bright orange LED is energized along with the vibration member. And, finally, a purple LED may be energized along with the vibration member if the actuation button is operated four times. And, as expressed above, the microcontroller may be programmed to operate the vibration member at various levels of intensity and for various time periods in accordance with a predetermined method of breathing techniques. In other words, users of the present invention, such as employees, may be trained in numerous types of breathing techniques that are then associated with corresponding colors of lights, intensity of vibrations, or combinations thereof.

In an embodiment, the electronic device 10 may be powered by a rechargeable battery 115, such as with a wireless magnetic charging cable 108 in which electric current passes through coiled wires to surround a magnet (known as an inductor) so as to make an electromagnet capable of passing voltage to a nearby receiver such as a battery. The battery may be secured at a position beneath the printed circuit board (PCB) using a battery retention bar 116 secured via screws 117 (FIG. 7). Reference character 119 is another component of the USB connector on the PC 138. The charging cable 108 may include a USB end 110 and a magnetic end 109 as would be understood in the art. The lower housing portion 101 may define a cavity 114 (FIG. 7) suitable for receiving the charging cable, the cavity being selectively covered by a charging port plug 104A, which may be peeled back as referenced by 104B.

According to the present invention, there may be multiple schemes of breathing techniques associated with respective modes by which the apparatus 10 may be used. More particularly, the apparatus 10 may be oriented into different modes of operation based on the number of times the mode selection button is depressed and respective modes may include varying intensities of the vibrator motor and LED illumination. Users may be trained to utilize different breathing techniques associated with the respective modes of operation and, as a result, breathing of a stressed user may be brought under control. The various breathing techniques associated with operation of the present apparatus 10 are illustrated schematically in FIGS. 17-22.

It is understood that while certain forms of this invention have been illustrated and described, it is not limited thereto except insofar as such limitations are included in the following claims and allowable functional equivalents thereof.

The invention claimed is:

1. A stress relieving apparatus, comprising:
   a breath ball assembly that includes a housing having a spherical configuration that defines an interior area;
   a plurality of light emitting diodes (LEDs) mounted in said interior area;
   a vibration member mounted in said interior area;
   a heating member mounted in said interior area;
   a microcontroller mounted in said interior area that is electrically connected to said plurality of LEDs, to said vibration member, and to said heating member, said microcontroller being programmed to energize said plurality of LEDs and said vibration member according to a plurality of user selected modes; and
   a pedestal assembly that includes a pedestal housing having a ring-shaped configuration that defines a central void and a plurality of apertures positioned radially about said central void, said pedestal assembly including a pumice stone removably situated in said central void and that is operable to emit a fragrance when heated;
   wherein said pedestal housing has an inwardly beveled configuration that is operable to selectively receive a portion of said housing of said breath ball assembly in a nested configuration.

2. The stress relieving apparatus as in claim 1, wherein said housing of said breath ball assembly includes an upper housing portion having a hemispherical configuration and a lower housing portion having a hemispherical configuration releasably coupled to said upper housing portion so as to, together, define a spherical or ball-shaped configuration defining said interior area.

3. The stress relieving apparatus as in claim 2, wherein said pedestal housing includes (1) a base portion having a circular configuration and to which a plurality of feet extends downwardly and (2) an upper portion coupled to and extending upwardly from said base portion, said upper portion having a ring-shaped configuration having an inner wall that slopes downwardly to one of a bottom wall or a ledge configured to support said pumice stone.

4. The stress relieving apparatus as in claim 3, wherein said inner wall of said upper portion includes an uppermost edge that is smaller than a diameter of an open end of said lower housing portion and is larger than a diameter of a closed end of said lower housing portion such that said lower housing portion is nested in said central void and said closed end is proximate said pumice stone.

5. The stress relieving apparatus as in claim 4, wherein said inner wall defines said plurality of apertures.

6. The stress relieving apparatus as in claim 1, wherein said microcontroller is programmed to:
 receive input data from a program control button mounted proximate to said housing of said breath ball assembly that is indicative of a number of times said program control button has been actuated; and
 energize said plurality of LEDs, said vibrator element, and said heating element according to predetermined sequences corresponding to said respective number of times said program control button has been actuated.

7. The stress relieving apparatus as in claim 6, wherein said microcontroller is programmed to:
 energize a white LED if said program control button has been actuated zero times;
 energize an amber LED and said vibration member if said program control button has been actuated one time;
 energize a pale blue LED and said vibration member if said program control button has been actuated two times;
 energize a bright orange LED and said vibration member if said program control button has been actuated three times; and
 energize a purple LED and said vibration member if said program control button has been actuated four times.

8. The stress relieving apparatus as in claim 7, wherein said microcontroller is programmed to determine an intensity by which said vibration member will vibrate for a predetermined amount of seconds.

9. The stress relieving apparatus as in claim 8, further comprising a rechargeable battery positioned in said interior area and electrically connected to said microcontroller.

10. The stress relieving apparatus as in claim 1, further comprising a printed circuit board (PCB) positioned in said interior area to which said plurality of LEDs, said vibration member, and said heating member are coupled, said PCB being electrically connected to a battery supported atop a plurality of battery support ribs.

11. A stress relieving apparatus, comprising:
 a breath ball assembly that includes a housing constructed of a transparent or translucent material and having a spherical configuration that defines an interior area;
 a plurality of light emitting diodes (LEDs) mounted in said interior area each having a color different from any other LED;
 a vibration member mounted in said interior area;
 a heating member mounted in said interior area;
 a microcontroller mounted in said interior area that is electrically connected to said plurality of LEDs, to said vibration member, and to said heating member, said microcontroller being programmed to energize said plurality of LEDs and said vibration member according to a plurality of user selected modes;
 a rechargeable battery electrically connected to said microcontroller;
 wherein said microcontroller is programmed to:
  receive input data from a program control button mounted proximate said housing that is indicative of a number of times said program control button has been actuated; and
  energize said plurality of LEDs, said vibrator element, and said heating element according to predetermined sequences corresponding to said respective number of times said program control button has been actuated; and
 a pedestal assembly that includes a pedestal housing having a ring-shaped configuration that defines a central void and a plurality of apertures positioned radially about said central void, said pedestal assembly including a pumice stone removably situated in said central void and that is operable to emit a fragrance when heated;
 wherein said pedestal housing has an inwardly beveled configuration that is operable to selectively receive a portion of said housing of said breath ball assembly in a nested configuration.

12. The stress relieving apparatus as in claim 11, wherein said housing of said breath ball assembly includes an upper housing portion having a hemispherical configuration and a lower housing portion having a hemispherical configuration releasably coupled to said upper housing portion so as to, together, define a spherical or ball-shaped configuration defining said interior area.

13. The stress relieving apparatus as in claim 12, wherein said pedestal housing includes (1) a base portion having a circular configuration and to which a plurality of feet extends downwardly and (2) an upper portion coupled to and extending upwardly from said base portion, said upper portion having a ring-shaped configuration having an inner wall that slopes downwardly to one of a bottom wall or a ledge configured to support said pumice stone.

14. The stress relieving apparatus as in claim 11, wherein said rechargeable battery includes a charging cable having a USB connector port.

15. The stress relieving apparatus as in claim 11, wherein said pedestal housing includes (1) a base portion having a circular configuration and to which a plurality of feet extends downwardly and (2) an upper portion coupled to and extending upwardly from said base portion, said upper portion having a ring-shaped configuration having an inner wall that slopes downwardly to one of a bottom wall or a ledge configured to support said pumice stone.

16. The stress relieving apparatus as in claim 15, wherein said inner wall of said upper portion includes an uppermost edge that is smaller than a diameter of an open end of said lower housing portion and is larger than a diameter of a closed end of said lower housing portion such that said lower housing portion is nested in said central void and said closed end is proximate said pumice stone.

17. The stress relieving apparatus as in claim 16, wherein said inner wall defines said plurality of apertures.

18. The stress relieving apparatus as in claim 11, wherein said microcontroller is programmed to:
 energize a white LED if said program control button has been actuated zero times;
 energize an amber LED and said vibration member if said program control button has been actuated one time;
 energize a pale blue LED and said vibration member if said program control button has been actuated two times;

energize a bright orange LED and said vibration member if said program control button has been actuated three times; and energize a purple LED and said vibration member if said program control button has been actuated four times.

19. The stress relieving apparatus as in claim 11, further comprising a printed circuit board (PCB) positioned in said interior area to which said plurality of LEDs, said vibration member, and said heating member are coupled, said PCB being electrically connected to a battery supported atop a plurality of battery support ribs.

* * * * *